US010998085B2

(12) United States Patent
Hsieh

(10) Patent No.: US 10,998,085 B2
(45) Date of Patent: May 4, 2021

(54) **METHOD FOR IDENTIFYING THE MOLECULAR CONFIGURATION OF GANODERIC ACID A FROM *GANODERMA LUCIDUM***

(71) Applicant: Tian-Jye Hsieh, Pingtung County (TW)

(72) Inventor: Tian-Jye Hsieh, Pingtung County (TW)

(*) Notice: Subject to any disclaimer, the term of this patent is extended or adjusted under 35 U.S.C. 154(b) by 339 days.

(21) Appl. No.: 16/143,292

(22) Filed: Sep. 26, 2018

(65) Prior Publication Data

US 2019/0303538 A1    Oct. 3, 2019

(30) Foreign Application Priority Data

Mar. 27, 2018  (TW) .................................. 10711052.6

(51) Int. Cl.
  *G16C 10/00*   (2019.01)
  *G01N 23/207*  (2018.01)
  *C07J 9/00*    (2006.01)

(52) U.S. Cl.
  CPC .............. *G16C 10/00* (2019.02); *C07J 9/005* (2013.01); *G01N 23/207* (2013.01); *G01N 2223/051* (2013.01)

(58) Field of Classification Search
  None
  See application file for complete search history.

(56) References Cited

U.S. PATENT DOCUMENTS

2015/0142398 A1* 5/2015 Miller, III .............. G16C 10/00
                                                        703/2

OTHER PUBLICATIONS

Grienke et al. ("Pharmacophore-based discovery of FXR-agonists. Part II: Identification of Bioactive Triterpenes from Ganodera Lucidum" Bioorganic & Medicinal Chemistry 19 (2011) p. 6779-6791) (Year: 2011).*
Cheng et al. ("DFT-based Quantitative Structure-Activity Relationship studies for Antioxidant Peptides", Struct Chem (2015), Springer Science+Business Media, NY, 2014, p. 739-747) (Year: 2015).*

* cited by examiner

*Primary Examiner* — Roy Y Yi
(74) *Attorney, Agent, or Firm* — AEON Law, PLLC; Adam L. K. Philipp; Shan Liao

(57) ABSTRACT

Disclosed is a method for identifying the molecular configuration of ganoderic acid A which comprises extracting ganoderic acid A from fruit bodies of *Ganoderma lucidum*, producing crystals of the ganoderic acid A, analyzing the crystals of the ganoderic acid A by X-ray structural analysis to obtain values of the three-dimensional coordinate of the crystals of the ganoderic acid A and using the values of the three-dimensional coordinate of the crystals of the ganoderic acid A obtained from the X-ray structural analysis as initial coordinates in the input to the calculation program of the B3LYP method included in the Gaussian 03 package software together with the 6-31G* basis set function of the density functional theory (DFT).

4 Claims, 4 Drawing Sheets

METHOD FOR IDENTIFYING THE MOLECULAR CONFIGURATION OF GANODERIC ACID A FROM *GANODERMA LUCIDUM*

FIELD OF THE INVENTION

The present invention relates to a method of identification of ganoderic acid A, and more particularly to a method for identifying the molecular configuration of ganoderic acid A extracted from *Ganoderma lucidum*.

BACKGROUND OF THE INVENTION

*Ganoderma lucidum*, a medicinal mushroom, belonging to the polyporaceae of aphyllophorales, is used in healthy food and medicine for more than 2000 years. In China and other Asian countries, *Ganoderma lucidum* is mainly used in preventing and treating various human diseases such as chronic bronchitis, hepatitis, hypertension, hypercholesterolemia, cancer, and immune diseases. According to the research, *Ganoderma lucidum* contains polysaccharides which have proven to inhibit the growth of cancer cells; moreover, *Ganoderma lucidum* can produce many oxygenated triterpenes with various biological functions such as cytotoxicity to hepatoma cells, inhibition of histamine release, inhibition of cholesterol synthesis and absorption, stimulation of platelet aggregation, as well as inhibition of thrombin-induced platelet aggregation.

Ganoderic acid, one of the oxygenated triterpenes, possesses various biological functions so that it can be used in healthcare or treatment of disease, including protecting the heart against necrosis or damage, promoting nerve cell growth and differentiation.

However, there is a lack of searching in the molecular structure of ganoderic acid A extracted from *Ganoderma lucidum*. It is well known that molecular structure plays a significant role in chemical properties of molecules. For instance, a slight change in biomolecular structure may alter the characteristics of cells, even leading to uncontrolled cell growth and tumor formation. Thus, it is important to determine the molecular structure of ganoderic acid A.

SUMMARY OF THE INVENTION

An objective of the present invention is to provide a ganoderic acid A with its molecular structure determined by X-ray crystallography, NMR spectroscopy, and density functional theory calculations.

The technical means adopted by the present invention to overcome the drawbacks in the prior art is to provide a ganoderic acid A. A method for identifying the molecular configuration of ganoderic acid A, comprising: extracting ganoderic acid A from *Ganoderma lucidum*; producing crystals of the ganoderic acid A; analyzing the crystals of the ganoderic acid A by X-ray structural analysis to obtain values of the three-dimensional coordinate of the crystals of the ganoderic acid A and using the values of the three-dimensional coordinate of the crystals of the ganoderic acid A obtained from the X-ray structural analysis as initial coordinates in the input to the calculation program of the B3LYP method included in the Gaussian 03 package software together with the 6-31G* basis set function of the density functional theory (DFT) to determine the molecular configuration of the ganoderic acid A.

In one embodiment of the present invention, the crystals of the ganoderic acid A are obtained by recrystallization followed by a crystal-growing process.

In one embodiment of the present invention, the crystals of the ganoderic acid A are analyzed by X-ray structural analysis on a SMART CCD diffract meter with Mo Kα radiation at 295K.

In one embodiment of the present invention, λ is 0.7107 Å on the SMART CCD diffract meter with Mo Kα radiation.

In one embodiment of the present invention, the ganoderic acid A is isolated from fruit bodies of *Ganoderma lucidum*.

By means of the technology of the present invention, the molecular configuration of ganoderic acid A extracted from *Ganoderma lucidum* has been determined so that ganoderic acid A can be applied in various areas such as being as a component of cosmetics, food, and health products.

DETAILED DESCRIPTION OF THE PREFERRED EMBODIMENTS

The preferred embodiments of the present invention are described below with reference to FIGS. 1-4. The description is only the explanation of the preferred embodiments and is not the limitation of the implementation of the present invention.

Figure 1:
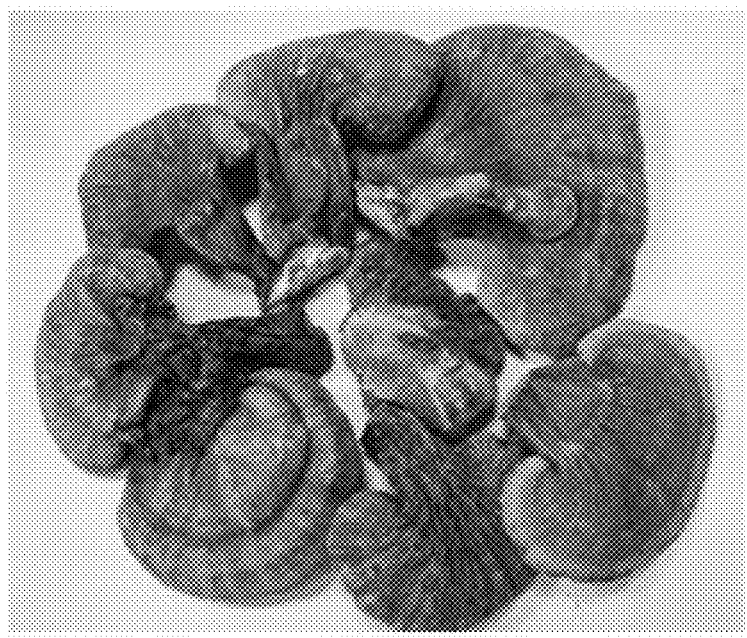
FIG. 1 shows a schematic view of *Ganoderma lucidum*.

The ganoderic acid A of the present invention is extracted from *Ganoderma lucidum* as shown in FIG. 1 having the following physico-chemical properties:

(a) $^1$H NMR (CDCl$_3$) δ: 0.98 (3H, d, J=6.4 Hz), 1.09 (3H, s), 1.13 (3H, s), 1.16 (3H, s), 1.35 (3H, d), 1.43 (3H, s), 1.52 (3H, s), 1.60 (2H, t), 1.85 (1H, dd, J=13.2 Hz), 1.95 (1H, m), 1.97 (1H, m), 1.98 (1H, m), 2.16 (1H, m), 2.2 (1H, m), 2.25 (1H, m), 2.34 (1H, dd, J=16 Hz), 2.56 (t, 2H), 2.59 (1H, dd), 2.60 (1H, dd, J=9.6 Hz), 2.67 (1H, d), 2.94 (1H, d), 3.11 (1H, dd), 3.30 (1H, qt), 4.95 (1H, dd, J=10 Hz), 5.25 (1H, dd, J=9.2 Hz);

(b) $^{13}$C-NMR (100 MHz, CDCl$_3$) δ: 36.0 (C-1), 34.6 (C-2), 216.1 (C-3), 46.7 (C-4), 48.9 (C-5), 29.6 (C-6), 68.7 (C-7), 161.5 (C-8), 139.9 (C-9), 38.3 (C-10), 199.7 (C-11), 52.4 (C-12), 47.0 (C-13), 54.7 (C-14), 72.2 (C-15), 36.9 (C-16), 48.6 (C-17), 17.5 (C-18), 19.6 (C-19), 33.1 (C-20), 19.7 (C-21), 49.9 (C-22), 209.0 (C-23), 47.1 (C-24), 35.6 (C-25), 178.2 (C-26), 17.6 (C-27), 20.3 (C-28), 27.2 (C-29), 20.8 (C-30);

(c) at room temperature (295 K), unit cell dimensions: a=7.1982(5) Å, b=12.8985(9) Å, c=9.3138(7) Å; α=90°, β=120°, γ=90°; space group=P2(1); volume: 4332.2(5) Å$^3$; Z=6; and Dcalc=1.188 Mgm$^{-3}$, wherein the physico-chemical properties are determined by X-ray crystallography, NMR spectroscopy, and density functional theory calculations.

Figure 2:
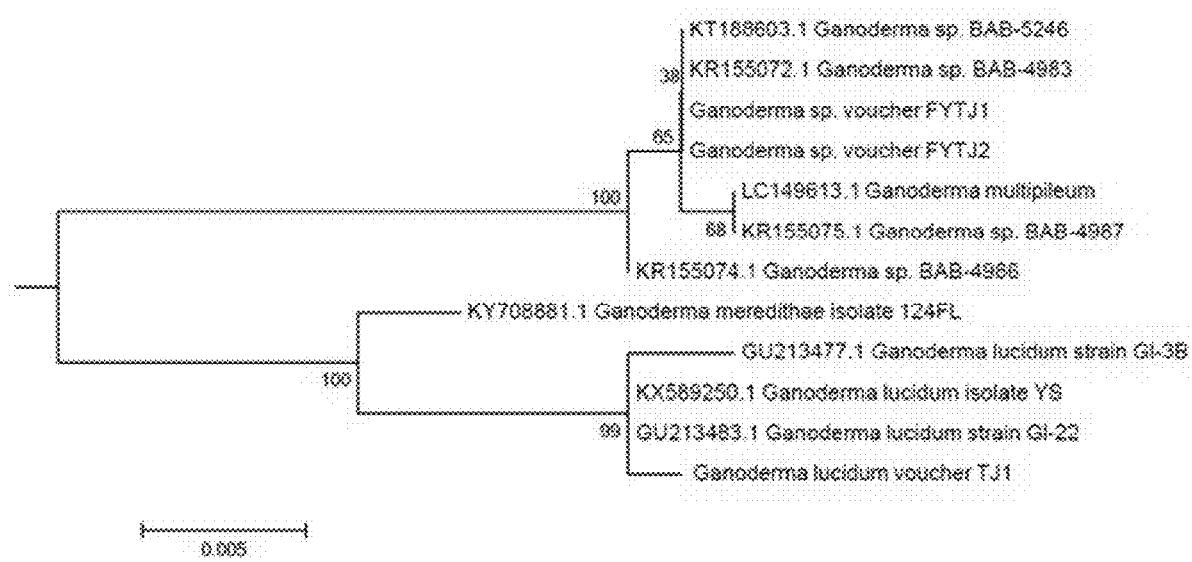
FIG. 2 is a maximal likelihood tree showing inferred phylogenetic relationships of fungal ITS gene sequences from cultured *Ganoderma lucidum* voucher TJ1 and NCBI Genbank.

Specifically, the ganoderic acid A is isolated from fruit bodies of *Ganoderma lucidum*. The fruit bodies are evidenced by the phylogenetic tree constructed with ITS sequence. The molecular identification is as follows:

Dried fruit bodies are cut into small pieces and ground with liquid nitrogen. Approximately 0.1 g ground sample is collected in a sterile 1.5 ml Eppendorf tube and followed by DNA extraction using the Qiagen plant Dneasy mini kit. Fungal DNAs extracted from the dried fruit bodies are amplified using primers ITS1F (5'-CTTGGTCATTTAGAG-GAAGTAA-3') and ITS4 (5'-TCCTCCGCTTATTGATA TGC-3'). The PCR reaction is carried out in a total volume of 50 μl containing 25 μl 2×PCR Master mix, 0.2 μM of each primer and 5 μl template DNA. The PCR program includes an initial denaturation at 95° C. and 72° C. for 3 minutes, with cooling at 4° C. Therefore, PCR products are checked by 1% agarose gel electrophoresis and sequencing. Taxonomic identification of the fungal sequence is blasted against National Center for Biotechnology information database. As shown in FIG. 2, maximal likelihood tree is constructed with MEGA6. The sequence of *Ganoderma lucidum* voucher TJ1 and reference sequences deposited in the GenBank database are aligned by ClustalW. The robustness of inferred topologies is tested by bootstrap analysis and 1000 resamplings of trees.

Ganoderic Acid a Extraction:

Dried fruit bodies of *Ganoderma lucidum* are crushed and extracted with MeOH. The MeOH extracts residue is placed on a silica gel column and eluted with EtOAc gradually enriched with MeOH to afford 10 fractions. Ganoderic acid A (78.0 mg) is isolated by silica gel column from fraction 3 with CHCl$_3$/MeOH 40:1 as elute solvent.

Production of Single Crystal of Ganoderic Acid A:

Single crystals of ganoderic acid A is obtained by recrystallization followed by a crystal-growing process. The recrystallization involves heating ganoderic acid A together with proper amount of methanol. Methanol vapor is allowed to slowly diffuse into the crystal-growing bottle until a perfect crystal is produced. The structure of the resulting single crystals is then analyzed by X-ray crystallography. Suitable crystals are selected, and then mounted on thin glass fibers using viscous oil. All measurements are made on a SMART CCD diffract meter with Mo Kα radiation with 0.7107 Å λ at 295K.

Figure 3:
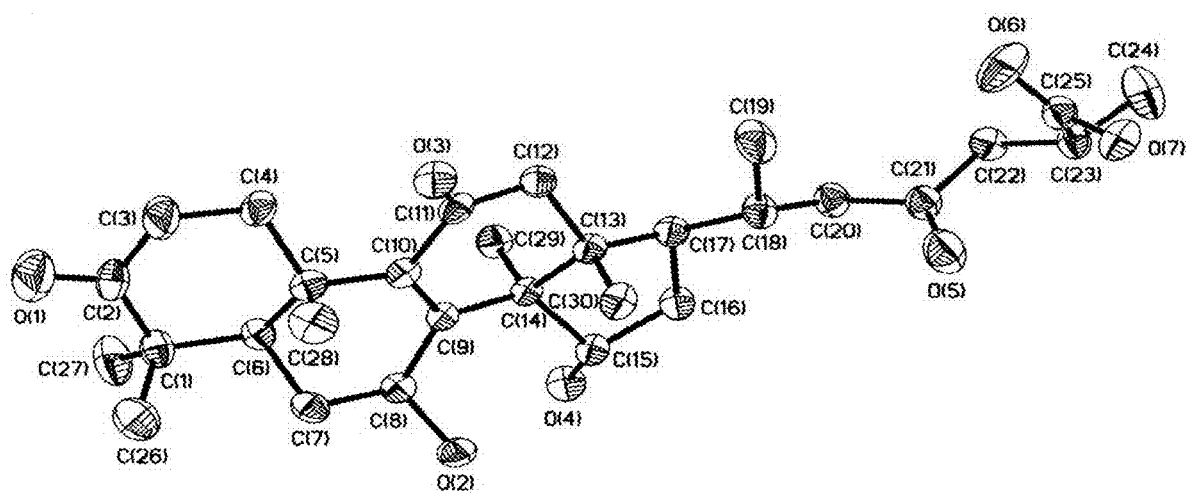
FIG. 3 is an ORTEP diagram of ganoderic acid A of the present invention.

As shown in FIG. 3, through structure analysis using X-ray crystallography, the ORTEP diagrams of ganoderic acid A is identified.

Figure 4:
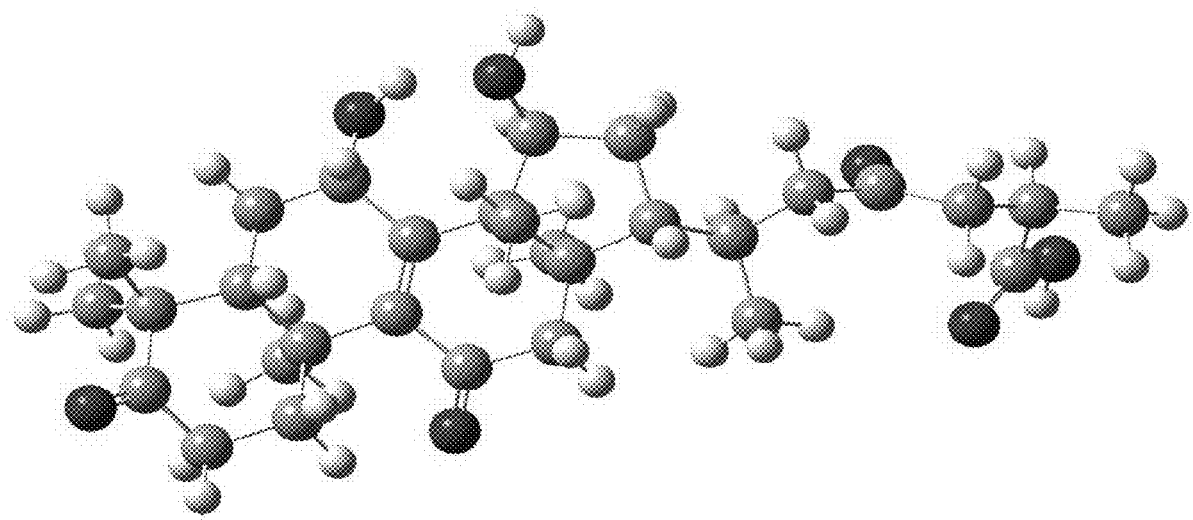
FIG. 4 is a theoretical calculation diagram of ganoderic acid A of the present invention.

Calculation Methods and Input:

All computations are carried out using the B3LYP method included in the Gaussian 03 package software together with the 6-31G* basis set function of the density (DFT) to understand structure features of the ganoderic acid A. The DFT theoretical calculation diagram of ganoderic acid A is shown in FIG. 4.

Result:

The obtained geometric structures of ganoderic acid A is shown as follows:

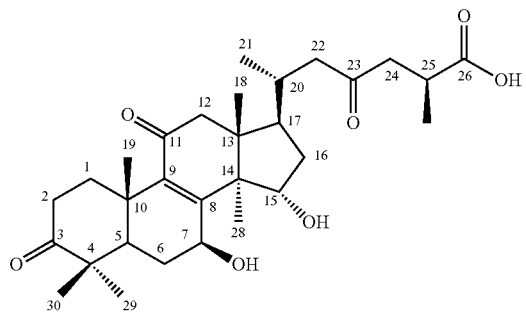

The values of the three-dimensional coordinate obtained from the X-ray structural analysis are used as initial coordinates in the input to the calculation program to compare the reliabilities and reasonableness of the theoretical methods used in the research.

Table 1 shows the data of crystals of ganoderic acid A and the atomic bond lengths of the best structure obtained by using B3LYP/6-31G*.

TABLE 1

| Atomic bond lengths (Å) | Crystallographic data | B3LYP/6-31G* |
|---|---|---|
| O1—C2 | 1.194(5) | 1.219 |
| O3—C11 | 1.214(4) | 1.226 |
| O5—C21 | 1.202(5) | 1.218 |
| O7—C25 | 1.305(5) | 1.353 |
| C1—C27 | 1.536(6) | 1.544 |
| C1—C6 | 1.572(5) | 1.570 |
| C3—C4 | 1.515(7) | 1.537 |
| C5—C10 | 1.523(5) | 1.554 |
| C5—C6 | 1.558(5) | 1.566 |
| C7—C8 | 1.524(5) | 1.522 |
| C9—C10 | 1.352(4) | 1.365 |
| C10—C11 | 1.513(5) | 1.504 |
| C12—C13 | 1.535(5) | 1.530 |
| C13—C17 | 1.554(5) | 1.565 |
| C14—C29 | 1.548(5) | 1.455 |
| C15—C16 | 1.538(5) | 1.549 |
| C17—C18 | 1.546(5) | 1.548 |
| C18—C19 | 1.528(6) | 1.539 |
| C21—C22 | 1.490(6) | 1.523 |
| C23—C25 | 1.510(5) | 1.526 |
| O2—C8 | 1.425(4) | 1.425 |
| O4—C15 | 1.430(4) | 1.442 |
| O6—C25 | 1.212(5) | 1.213 |
| C1—C2 | 1.524(6) | 1.546 |
| C1—C26 | 1.542(7) | 1.552 |
| C2—C3 | 1.434(7) | 1.518 |
| C4—C5 | 1.543(5) | 1.555 |
| C5—C28 | 1.545(5) | 1.552 |
| C6—C7 | 1.522(5) | 1.528 |
| C8—C9 | 1.531(5) | 1.533 |
| C9—C14 | 1.528(5) | 1.539 |
| C11—C12 | 1.487(6) | 1.528 |
| C13—C30 | 1.534(5) | 1.402 |
| C13—C14 | 1.564(4) | 1.576 |
| C14—C15 | 1.553(4) | 1.549 |
| C16—C17 | 1.549(5) | 1.565 |
| C18—C20 | 1.514(6) | 1.403 |
| C20—C21 | 1.505(5) | 1.527 |
| C22—C23 | 1.518(5) | 1.529 |
| C23—C24 | 1.525(6) | 1.521 |

The calculations of ganoderic acid A are in closest agreement with the experiment and are also molecule predicted by DFT calculations. The atomic torsion angle of ganoderic acid A obtained by X-ray crystallography structural analysis and theoretical calculations is shown in Table 2.

TABLE 2

| Atomic torsion angle (°) | Crystallographic data | B3LYP/6-31G* |
|---|---|---|
| C2—C1—C27 | 106.8(4) | 107.8 |
| C27—C1—C26 | 108.7(4) | 107.5 |
| C27—C1—C6 | 108.4(3) | 109.4 |
| O1—C2—C3 | 117.2(5) | 120.9 |
| C3—C2—C1 | 123.5(4) | 117.6 |
| C3—C4—C5 | 112.8(4) | 112.6 |
| C10—C5—C28 | 109.3(3) | 107.1 |
| C10—C5—C6 | 107.3(3) | 107.9 |
| C28—C5—C6 | 113.6(3) | 115.0 |
| C7—C6—C1 | 113.1(3) | 114.2 |
| C6—C7—C8 | 110.3(3) | 109.5 |
| O2—C8—C9 | 111.1(3) | 112.8 |
| C10—C9—C14 | 121.4(3) | 120.4 |
| C14—C9—C8 | 116.0(2) | 117.0 |
| C9—C10—C5 | 124.4(3) | 123.5 |
| O3—C11—C12 | 119.4(4) | 118.1 |
| C12—C11—C10 | 119.5(3) | 119.6 |
| C30—C13—C12 | 108.1(3) | 108.2 |
| C12—C13—C17 | 118.3(3) | 117.8 |
| C12—C13—C14 | 107.6(3) | 107.1 |
| C9—C14—C29 | 104.7(3) | 104.4 |
| C29—C14—C15 | 107.4(7) | 107.5 |
| C29—C14—C13 | 113.4(3) | 113.7 |
| O4—C15—C16 | 109.8(3) | 112.9 |
| C16—C15—C14 | 103.2(3) | 104.0 |
| C18—C17—C16 | 113.0(3) | 112.7 |
| C16—C17—C13 | 102.5(3) | 102.3 |
| C20—C18—C17 | 111.1(3) | 110.1 |
| C21—C20—C18 | 113.2(3) | 112.1 |
| O5—C21—C20 | 120.6(4) | 120.9 |
| C21—C22—C23 | 114.7(3) | 113.3 |
| C25—C23—C24 | 109.4(4) | 109.6 |
| O6—C25—O7 | 123.3(4) | 122.4 |
| O7—C25—C23 | 112.0(3) | 120.0 |
| C2—C1—C26 | 107.3(4) | 107.2 |
| C2—C1—C6 | 111.2(3) | 110.2 |
| C26—C1—C6 | 114.3(4) | 114.5 |
| O1—C2—C1 | 119.3(5) | 121.4 |
| C2—C3—C4 | 118.4(5) | 114.1 |
| C10—C5—C4 | 110.0(3) | 110.7 |
| C4—C5—C28 | 110.8(3) | 110.0 |
| C4—C5—C6 | 105.7(3) | 106.1 |
| C7—C6—C5 | 110.1(3) | 109.7 |
| C5—C6—C1 | 117.0(3) | 118.3 |
| O2—C8—C7 | 110.6(3) | 107.1 |
| C7—C8—C9 | 113.0(3) | 113.0 |
| C10—C9—C8 | 122.1(3) | 122.0 |
| C9—C10—C11 | 118.6(3) | 119.4 |
| C11—C10—C5 | 117.0(3) | 116.9 |
| O3—C11—C10 | 121.0(4) | 122.3 |
| C11—C12—C13 | 110.8(3) | 111.0 |
| C30—C13—C17 | 109.9(3) | 109.6 |
| C30—C13—C14 | 110.6(3) | 111.7 |
| C17—C13—C14 | 102.2(2) | 102.3 |
| C9—C14—C15 | 121.3(3) | 120.6 |
| C9—C14—C13 | 110.9(2) | 111.8 |
| C15—C14—C13 | 99.4(2) | 99.2 |
| O4—C15—C14 | 115.1(3) | 111.9 |
| C15—C16—C17 | 108.0(3) | 107.4 |
| C18—C17—C13 | 117.7(3) | 119.0 |
| C20—C18—C19 | 109.5(4) | 108.9 |
| C19—C18—C17 | 114.2(3) | 114.0 |
| O5—C21—C22 | 121.1(4) | 121.6 |
| C22—C21—C20 | 118.3(3) | 117.6 |
| C25—C23—C22 | 111.7(3) | 109.7 |
| C22—C23—C24 | 111.3(4) | 112.2 |
| O6—C25—C23 | 124.5(4) | 125.8 |

Please refer to Table 3, the overall B3LYP/6-31G* calculation of the molecular structures of ganoderic acid A is in excellent agreement with experimental data.

TABLE 3

| | Ganoderic acid A |
|---|---|
| Empirical formula | $C_{30}H_{44}O_7$ |
| Formula weight | 516.65 |
| Crystal system | hexagonal |
| Space group | P2(1) |
| Unit cell dimensions | a = 7.1982(5) Å |
| | b = 12.8985(9) Å |
| | c = 9.3138(7) Å |
| β(°) or γ(°) | 120 |
| volume (Å$^3$) | 4332.2(5) |
| Z (atoms/unit) | 6 |
| $D_{calc}$/Mgm$^{-3}$ | 1.188 |
| T(K) | 295(2) |
| Absorption coefficient | 0.083 |
| F(000) | 1680 |
| θ range (deg) | 2.09~27.50 |
| Crystal size | 0.50 × 0.50 × 0.35 mm$^3$ |
| Index range | h(−14~8) |
| | k(−4~14) |
| | l(−50~51) |
| Reflection collection | 19223 |
| Independent reflection | 6564(R(int) = 0.0436 |
| Absorption correction | Semi-empirical |
| Max. and min. transmission | 0.9715 and 0.9596 |
| Data/restraints/parameters | 6564/1/314 |
| GOF on F$^2$ | 1.064 |
| Final R indices [I > 2σ(I)] | R1 = 0.0797; |
| | WR2 = 0.1829 |
| R indices(all data) | R1 = 0.1070; |
| | WR2 = 0.2003 |
| Largest diff. peak/hole[e Å$^{-3}$] | 0.417/−0.212 |

The above description is only the explanation of the preferred embodiments of the present invention. However, a person with ordinary skill in the art may make various modifications to the present invention. Those modifications shall still fall within the spirit and the scope defined by the appended claims.

What is claimed is:

1. A method for identifying the molecular configuration of ganoderic acid A, comprising:
    extracting ganoderic acid A from *Ganoderma lucidum*;
    producing crystals of the ganoderic acid A;
    analyzing the crystals of the ganoderic acid A by X-ray structural analysis to obtain values of the three-dimensional coordinate of the crystals of the ganoderic acid A; and
    using the values of the three-dimensional coordinate of the crystals of the ganoderic acid A obtained from the X-ray structural analysis as initial coordinates in the input to the calculation program of the B3LYP method included in the Gaussian 03 package software together with the 6-31G* basis set function of the density functional theory (DFT) to determine the molecular configuration of the ganoderic acid A,
    wherein, the *Ganoderma lucidum* is subjected to DNA extraction before extracting the ganoderic acid, the extracted DNA of the *Ganoderma lucidum* uses the primer ITS1F shown in SEQ ID NO:1 and the primer ITS4 shown in SEQ ID NO:2 undergoes polymerase chain reaction and then DNA sequencing is performed to ensure that it is *Ganoderma lucidum*.

2. The method of claim 1, wherein the crystals of the ganoderic acid A are obtained by recrystallization followed by a crystal-growing process.

3. The method of claim 1, wherein the crystals of the ganoderic acid A are analyzed by X-ray structural analysis on a SMART CCD diffract meter with Mo Kα radiation at 295K.

4. The method of claim 3, wherein $\lambda$ is 0.7107 Å on the SMART CCD diffract meter with Mo K$\alpha$ radiation.

\* \* \* \* \*